United States Patent [19]
Baer et al.

[11] 3,963,715
[45] June 15, 1976

[54] SUBSTITUTED PYRAZINES

[75] Inventors: Donald R. Baer; Allan Cairncross, both of Wilmington, Del.; Michael Smith, North Tonawanda, N.Y.

[73] Assignee: E. I. Du Pont de Nemours & Company, Wilmington, Del.

[22] Filed: May 25, 1973

[21] Appl. No.: 363,804

Related U.S. Application Data
[63] Continuation-in-part of Ser. No. 240,296, March 31, 1972, abandoned.

[52] U.S. Cl. .................................. 260/250 BN
[51] Int. Cl.² ............................... C07D 241/14
[58] Field of Search ........................ 260/250 BN

[56] References Cited
UNITED STATES PATENTS

| | | | |
|---|---|---|---|
| 2,200,689 | 5/1940 | Echert et al. | 260/250 BN |
| 3,763,161 | 10/1973 | Hortter | 260/250 BN |
| 3,814,757 | 6/1974 | Donald | 260/250 BN |

OTHER PUBLICATIONS
Begland et al. "J. A. C. S." vol. 93 pp. 4953–4955 (1971).

*Primary Examiner*—Raymond V. Rush
*Assistant Examiner*—D. B. Springer

[57] ABSTRACT

Tetracyanopyrazine reacts with aromatic amines to give products of the formula

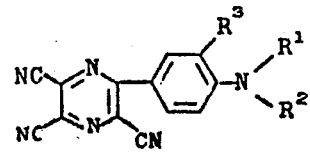

wherein $R^1$ and $R^2$, alike or different, are alkyl of 1-12 carbon atoms, cycloalkyl of 3-7 carbon atoms, phenyl, p-(lower alkyl)-phenyl, p-(lower alkoxy)phenyl, p-(lower alkylthio)phenyl, p-chlorophenyl, p-bromophenyl, aralkyl, aroxyalkyl, aroyloxyalkyl, acyloxyalkyl and trifluoroacetoxyalkyl each of up to 15 carbon atoms, and wherein aryl is phenyl substituted with up to 2 lower alkyl groups, and with the proviso that the alkylene group of aroyloxyalkyl, acyloxyalkyl and trifluoroacetoxyalkyl is at least 2 carbon atoms in length;

$R^3$ is hydrogen, lower alkyl, alkoxy or alkylthio of 1-6 carbons.

The cyano groups of the pyrazine ring can be converted to acid, ester or amide groups by conventional reactions.

The compounds are useful as dyes and pigments.

10 Claims, No Drawings

SUBSTITUTED PYRAZINES

RELATED APPLICATIONS

This application is a continuation-in-part of application Ser. No. 240,296 filed Mar. 31, 1972, and now abandoned.

FIELD OF THE INVENTION

This invention relates to novel pyrazine derivatives and to methods of making the same.

BACKGROUND OF THE INVENTION

Per-compounds have been known for a number of years. For example, tetrafluoroethylene and other perhalogenated compounds are widely known and used in polymers, stable fluids and numerous other applications. Percyano and polycyano compounds, e.g., tetracyanoethylene, are also known and their chemistry reviewed in Chapter 9 in Z. Rappaport, "The Chemistry of the Cyano Group", John Wiley and Sons, Interscience Publishers, 1970. These polycyano compounds frequently undergo nucleophilic displacement reactions unique to compounds highly substituted by cyano groups. No art appears to exist, however, disclosing the compounds of the present invention.

Tetracyanopyrazine is described and claimed in Hartter U.S. Pat. No. 3,763,161. It serves as the starting material for making the novel tricyano[(p-disubstituted-amino)phenyl]-pyrazines of the present invention. These compounds are useful as dyes for synthetic and natural fibers and as pigments in synthetic resin finishes.

SUMMARY OF THE INVENTION

The compounds of the present invention have the formula:

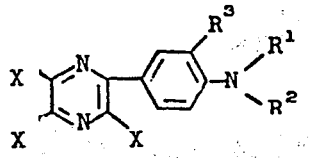

wherein:
X is CN, $CONH_2$, $CO_2H$ or $CO_2$(lower alkyl),
$R^1$ and $R^2$, alike or different, are alkyl of 1–12 carbon atoms, cycloalkyl of 3–7 carbon atoms, phenyl, p-(lower alkyl)phenyl, p-(lower alkoxy)phenyl, p-(lower alkylthio)phenyl, p-chlorophenyl, p-bromophenyl,
aralkyl, aroxyalkyl, aroyloxyalkyl, acyloxyalkyl and trifluoroacetoxyalkyl each of up to 15 carbon atoms, and wherein aryl is phenyl substituted with up to 2 lower alkyl groups, and with the proviso that the alkylene group of aroyloxyalkyl, acyloxyalkyl and trifluoroacetoxyalkyl is at least 2 carbon atoms in length; and
$R^3$ is hydrogen, lower alkyl, alkoxy or alkylthio of 1–6 carbons.

This invention also comprises a method of making the above compounds which comprises the essential step of contacting and reacting tetracyanopyrazine,

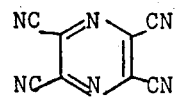

with an aromatic amine having the formula

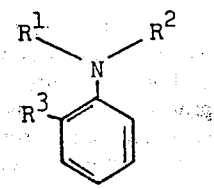

wherein $R^1$, $R^2$ and $R^3$ have the same meaning as hereinabove, in an inert solvent at a temperature in the range of 50 to 175°C, preferably 100° to 150°C. The cyano group can be converted to acid, amide or ester groupings, if desired, by conventional methods.

DETAILED DESCRIPTION OF THE INVENTION

The compounds of the present invention are made by the reaction of tetracyanopyrazine with an N,N-disubstituted aromatic amine according to the equation:

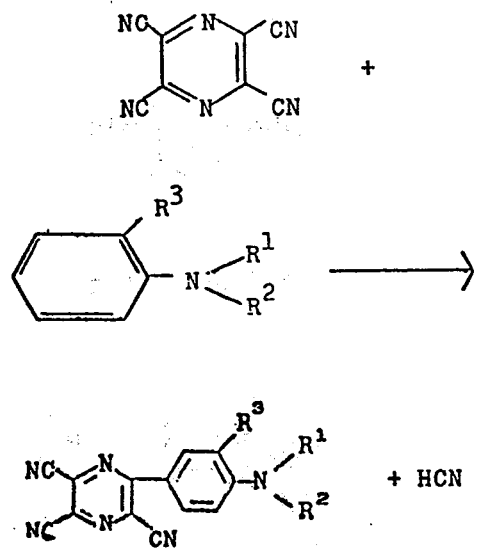

wherein $R^1$, $R^2$ and $R^3$ have the meaning given hereinabove followed by post-reaction of the cyano group, if required.

In a preferred group of compounds, $R^3$ is hydrogen, $R^1$ and $R^2$ are preferably lower alkyl, phenyl or 2-(benzoyloxy)-ethyl, and X is preferably CN.

When $R^1$ and $R^2$ are aroyloxyalkyl, acyloxyalkyl and trifluoroacetyloxyalkyl, the alkylene chain attached to the aroyloxy, acyloxy and trifluoroacetoxy should be at least two carbon atoms in length.

The tetracyanopyrazine and aromatic amine reactants are generally used in equimolar amounts although an excess of either starting material may be employed and is not critical. Preferably an excess of the aromatic amine is employed to ensure complete reaction of the tetracyanopyrazine.

Reaction is carried out in an organic solvent inert to the reactants, and one in which tetracyanopyrazine is soluble. It is possible to employ an excess of the aromatic amine as a solvent and reactant. Suitable solvents include benzene, chlorobenzene, dioxane, tetrahydrofuran, 1,2-dimethoxyethane, di-n-butyl ether, 2-methoxyethyl ether (diglyme), ethyl acetate, butyl acetate, acetonitrile, dimethylformamide, dimethylacetamide, dimethylsulfoxide, and hexamethylphosphoramide.

The pressure at which the reaction is conducted is not critical, and is conveniently atmospheric pressure, although higher or lower pressures can be employed.

The reaction proceeds at a convenient rate over a wide temperature range, e.g., from 50°–175°C, but preferably is carried out at temperatures from 100°–150°C.

Since HCN is produced as a by-product of the reaction, adequate safety precautions must be taken to ensure its safe disposal.

Examples of products obtainable by the process of this invention include the compounds shown below in column II, obtained by reaction of the tertiary aromatic amine of column I with tetracyanopyrazine according to the disclosed process.

| Column I | Column II |
|---|---|
| 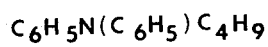 | 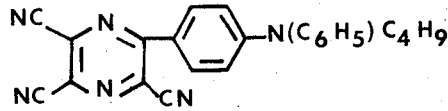 |
| 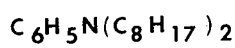 | 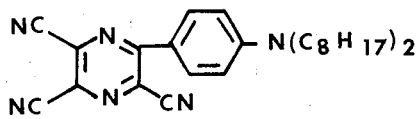 |
| 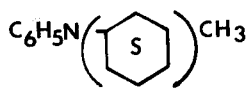 | 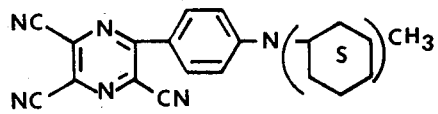 |
| 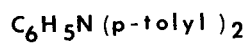 | 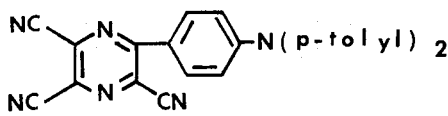 |
| 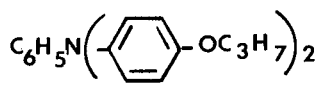 | 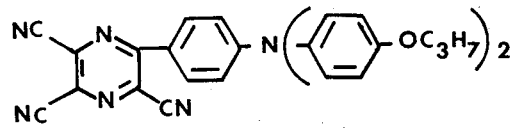 |
|  | 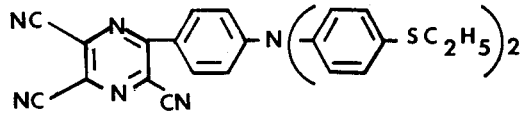 |
| 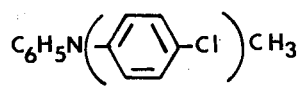 | 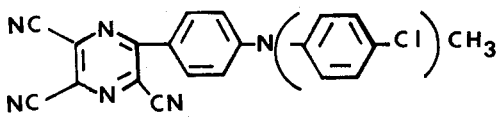 |
| 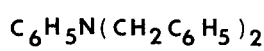 | 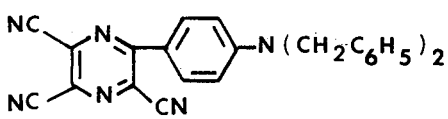 |
| 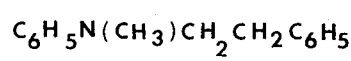 | 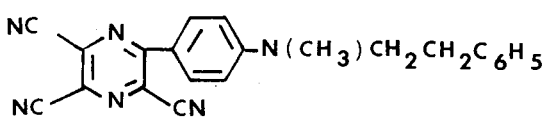 |

| Column I | Column II |
|---|---|
|  $C_6H_5N(CH_2CH_2O_2CC_3H_7)_2$ | 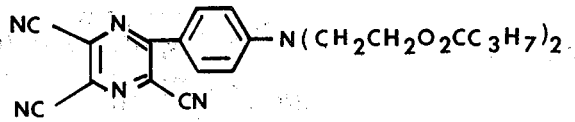 |
| 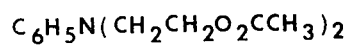 $C_6H_5N(CH_2CH_2O_2CCH_3)_2$ | 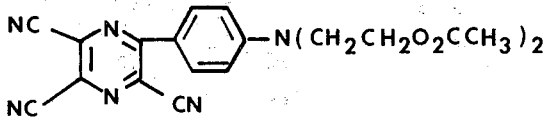 |
| 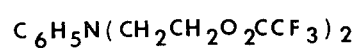 $C_6H_5N(CH_2CH_2O_2CCF_3)_2$ | 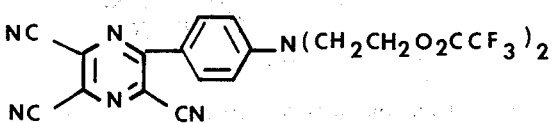 |
| 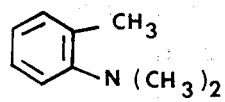 | 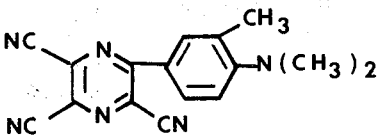 |
| 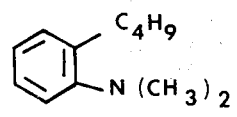 | 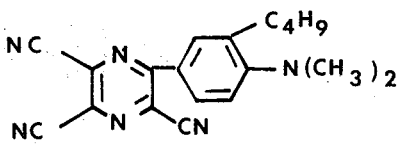 |
| 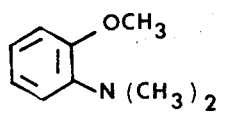 | 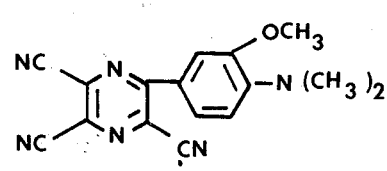 |
| 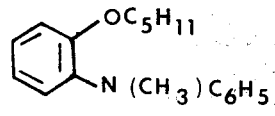 | 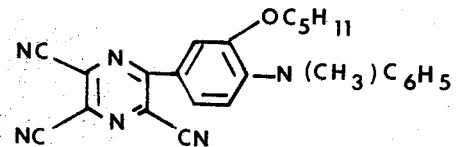 |
| 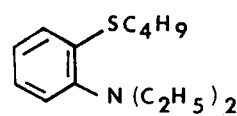 | 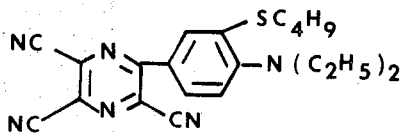 |
| 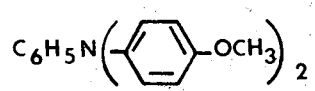 | 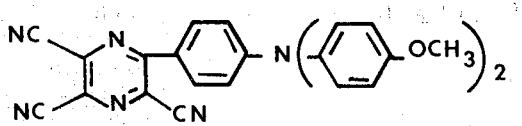 |
| 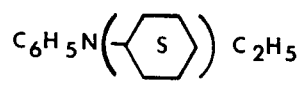 | 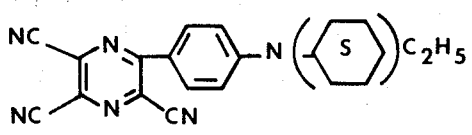 |

| Column I | Column II |
|---|---|
|  | 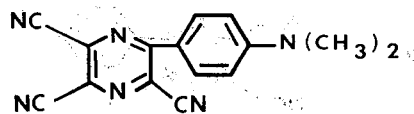 |
| 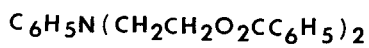 | 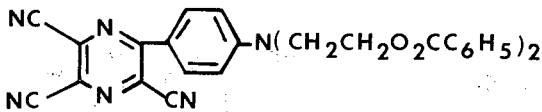 |
|  | 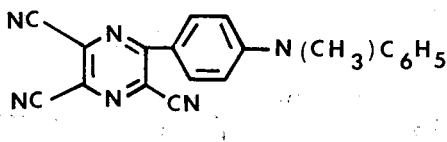 |

In like manner reaction of the following tertiary aromatic amines with tetracyanopyrazine gives the corresponding tricyano[(p-disubstituted-amino)phenyl]-pyrazine.

$C_6H_5N(CH_3)C_2H_5$
$C_6H_5N(C_2H_5)_2$
$C_6H_5N(CH_3)C_3H_7$
$C_6H_5N(C_2H_5)C_3H_7$
$C_6H_5N(C_3H_7)_2$
$C_6H_5N(CH_3)C_3H_7$-iso
$C_6H_5N(C_2H_5)C_3H_7$-iso
$C_6H_5N(C_3H_7$-iso$)_2$
$C_6H_5N(C_2H_5)C_4H_9$
$C_6H_5N(C_2H_5)C_4H_9$-iso
$C_6H_5N(C_5H_{11})_2$
$C_6H_5N(C_5H_{11})C_5H_{11}$-iso

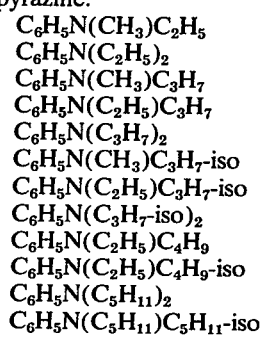

$C_6H_5N(CH_3)CH_2CH(CH_3)CH_2CH_3$

$C_6H_5N(C_2H_5)C_6H_5$
$C_6H_5N(C_6H_5)_2$
$C_6H_5N(CH_3)CH_2CH_2OC_6H_3(CH_3)_2$-2,4
$C_6H_5N(CH_3)CH_2CH_2OC_6H_4(CH_3)$-p
$C_6H_5N(CH_3)C_{12}H_{25-n}$
$C_6H_5N(CH_3)CH_2CH_2O_2CC_6H_5$
$C_6H_5N(CH_3)CH_2CH(O_2CCH_3)CH_3$
$C_6H_5N(C_2H_5)CH_2CH(O_2CCH_3)CH_3$
$C_6H_5N(CH_3)CH_2CH_2CH(O_2CC_6H_5)C_3H_7$
$C_6H_5N(CH_3)CH_2CH_2CH_2C(CH_3)_2O_2CCH_3$
$C_6H_5N(CH_3)CH_2CH_2CH_2OC_6H_5$
$C_6H_5N(CH_3)CH_2CH(CH_3)OC_6H_5$
$C_6H_5N(C_2H_5)CH_2CH_2OC_6H_5$

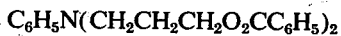

$C_6H_5N(CH_2CH_2CH_2O_2CC_6H_5)_2$

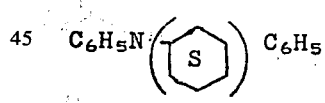

$C_6H_5N(CH_3)C_6H_4(i-C_3H_7)$-p
$C_6H_5N(CH_3)C_6H_4(OCH_3)$-p
$C_6H_5N(CH_3)C_6H_4Br$-p
$C_6H_5N(CH_3)C_6H_4(OC_4H_9)$-p
$C_6H_5N(CH_3)C_6H_4(C_2H_5)$-p
$C_6H_5N(CH_3)C_6H_4(OC_6H_{13})$-p
$C_6H_5N(C_6H_5)CH_2CH_2CH_2CH_2OC_6H_5$
$C_6H_5N(C_6H_5)CH_2CH_2C_6H_5$
$C_6H_5N(C_6H_5)CH_2C_6H_5$
$C_6H_5N(CH_3)C_6H_4(SC_3H_7)$-p
$C_6H_5N(C_6H_5)C_5H_{11}$
$C_6H_5N(CH_3)C_6H_4(OCH_2CH(C_2H_5)CH_2CH_3)$-p

These reactions give the novel products of formula I with X = CN. The compounds of the invention where X = $CONH_2$, $CO_2H$ and $CO_2$(lower alkyl) are readily obtained from the tricyanopyrazine derivatives by applying known hydrolytic procedures for conversion of nitrile groups to amides, carboxylic acids and esters. For example, hydrolysis of

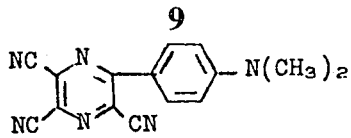

with concentrated sulfuric acid readily gives the corresponding pyrazine,

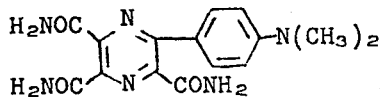

($X = CONH_2$) as shown in Example 4 below. Similar hydrolysis of the pyrazines shown in Column II give the corresponding novel pyrazines, $X = CONH_2$. Alternatively, basic hydrolysis as described in Wagner & Zook, "Synthetic Organic Chemistry", John Wiley & Sons, Inc., New York, 1953, p. 570, for conversion of nitriles to the corresponding amides, may be employed to obtain the tricarboxamido pyrazines ($X = CONH_2$) from the corresponding tricyanopyrazines of Column II.

More vigorous hydrolysis of the tricyanopyrazines ($X = CN$) with either acid or base gives the corresponding tricarboxylic acid pyrazines ($X = CO_2H$). For example, refluxing of the pyrazine of Example 1 below with an aqueous solution of sulfuric acid or sodium hydroxide gives the corresponding tricarboxylic acid pyrazine ($X = CO_2H$, $R^3 = H$, $R^1 = R^2 = CH_3$) described in Example 5. Alternatively, this pyrazine may be obtained from the corresponding tricarboxamido pyrazine ($X = CONH_2$) by refluxing with a potassium hydroxide solution as described in Example 5. In a similar way, the tricyanopyrazines of Column II may be converted to the corresponding novel tricarboxylic acid pyrazines ($X = CO_2H$).

The novel tricyanopyrazines of Column II also serve as starting materials for the preparation of the corresponding trialkoxycarbonyl pyrazines (formula I, $X = CO_2$(lower alkyl)). For example, hydrolysis of nitriles to carboxylic esters may be carried out by heating the nitrile with an alcohol and sulfuric or hydrochloric acid and hydrolysis of the imino ester intermediate with water (Wagner & Zook, ibid., p. 485). Thus, the pyrazine of Example 1 below is converted to the corresponding triethoxycarbonyl pyrazine (I, $x = CO_2C_2H_5$, $R^3 = H$, $R^1 = R^2 = CH_3$) by heating with ethanol and sulfuric acid. In the same manner, the other tricyanopyrazines of Column II are converted to the corresponding triethoxycarbonyl pyrazines. Replacement of the ethanol with another alcohol, e.g., methanol, 1-propanol, 1-hexanol, 2-butanol, etc., gives the corresponding ester.

The trialkoxycarbonyl pyrazines may also be prepared from the corresponding tricarboxylic acid pyrazines by heating with an alcohol in the presence of an acid catalyst. Thus, I ($X = CO_2C_2H_5$, $R^3 = H$, $R^1 = R^2 = CH_3$) is obtained from the corresponding tricarboxylic acid ($X = CO_2H$) by heating the acid with ethanol in the presence of sulfuric acid. In the same manner, the other tricarboxylic acid pyrazines of this invention are converted to the corresponding trialkoxycarbonyl pyrazines.

In the case of the pyrazines of formula I where $R^1$ and/or $R^2$ = aroyloxyalkyl, acyloxyalkyl and trifluoroacetoxy alkyl, (e.g., the pyrazine of Example 3 below) hydrolysis or alcoholysis of the tricyanopyrazine to obtain the corresponding pyrazines of formula I where $X = CONH_2$, or $CO_2H$ and $CO_2$-(lower alkyl) may cause hydrolysis of the ester group. For example, hydrolysis of

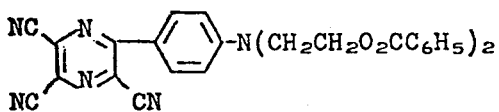

with concentrated sulfuric acid gives the corresponding pyrazine,

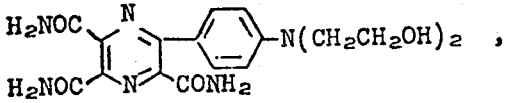

wherein the ester groups are hydrolyzed to the hydroxyalkyl derivatives. The pyrazine,

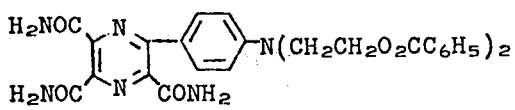

is readily obtained by benzoylation of the hydroxyalkyl derivative, e.g., with benzoyl chloride in pyridine. In the same way, other acyl derivatives are obtained by acylation of the hydroxyalkyl intermediate with acetyl chloride, butyryl chloride, p-methoxybenzoyl chloride, etc.

In this specification and the appended claims, the term "lower alkyl" denotes an alkyl group, linear or branched of from 1 to 6 carbon atoms.

An aryl group is a group or radical derived from an aromatic hydrocarbon having only 6-membered rings of carbon atoms by removal of a hydrogen atom attached to ring or nuclear carbon atom.

An aralkyl radical is a radical derived from an aromatic hydrocarbon having at least 1 alkyl substituent by removal of a hydrogen atom from an aliphatic carbon atom.

An aroyl group is defined as an ArCO group wherein Ar denotes an aryl radical.

An acyl group is defined as an $R^4CO-$ group wherein $R^4$ is an alkyl radical.

EMBODIMENTS OF THE INVENTION

The following examples illustrate specific embodiments of the invention. NMR spectra were obtained in deuterated dimethylsulfoxide solution with tetramethylsilane as internal standard.

EXAMPLE 1

6-[p-(Dimethylamino)phenyl]-2,3,5-pyrazinetricarbonitrile

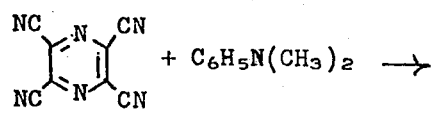

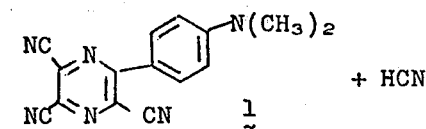

Three grams (10.0 mmoles) of an equimolar mixture of tetracyanopyrazine (TCP) and N,N-dimethylaniline was dissolved in 20 ml of dimethylsulfoxide and the solution was heated for 8 hours at 100°C under nitrogen, cooled overnight, and poured onto 500 ml of ice water.

The sticky crystals (2.78 g) were collected, dried, recrystallized twice from toluene, pulverized, and dried at 80°C (0.5 atm) to remove toluene of crystallization to give 1.57 g of deep red-brown 6-[p-(dimethylamino)phenyl]-2,3,5-pyrazinetricarbonitrile, mp 198.2-199.6°C.

Anal. Calcd for $C_{15}H_{10}N_6$: C, 65.68; H, 3.68; N, 30.64. Found: C, 65.95; H, 4.17; N, 30.55; C, 65.60; H, 3.74; N, 30.92.

IR (KBr): 3.28 μ (aryl CH), 3.39, 3.46 μ (aliphatic CH), 4.46 μ (nitrile), 6.21, 6.59, 12.07 μ (p-disubstituted benzene).

UV $\lambda_{max}^{EtOH}$: 445 nm (k 107, ε 28,900), 283 (k 39.6), 267 (k 40.3).

Mass Spec.: molecular ion m/e 274.0950 (calcd $C_{15}H_{10}N_6$: 274.0966).

NMR: δ 8.10 and 6.94 (4.0 H, AB pattern, J = 9 Hz), 3.11 (5.6 H, singlet).

EXAMPLE 2

6-[p-(Methylphenylamino)phenyl]-2,3,5-pyrazinetricarbonitrile

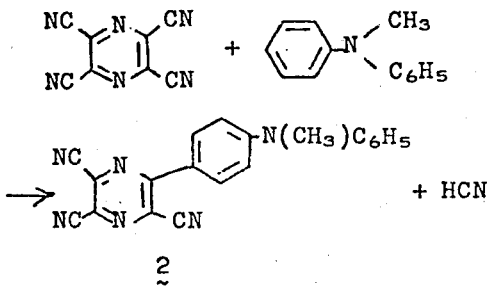

2

A mixture of 18 g of tetracyanopyrazine and 18.3 g of N-methyl-N-phenylaniline in 200 ml of dimethylsulfoxide was heated at 100°C for 21 hours, the solution was cooled and poured onto 6 liters of ice water to give a sticky precipitate. The mixture was extracted with ethyl acetate. The ethyl acetate solution was back-extracted with water, dried over sodium sulfate and concentrated to give a dark brown solid. Unreacted tetracyanopyrazine was removed by recrystallization of the solid from toluene, from which TCP was the first to crystallize. The toluene solution was concentrated and the residue was rinsed with hexane to partially remove unreacted N-methyl-N-phenylaniline. The residue was dissolved in aqueous tetrahydrofuran (THF) (75% tetrahydrofuran) at 50°C, the THF removed by distillation, and the residual solid washed with water to remove water-soluble by-products. The remaining product was chromatographed on a column of neutral silicic acid using hexane/benzene/ acetonitrile eluents. Red fractions were combined, concentrated, and the product recrystallized from heptane-toluene to give 3.02 g of red-purple 6-[p-(methylphenylamino)phenyl]-2,3,5-pyrazinetricarbonitrile, mp 187.3°-1.88.8°C after drying at 111°C (0.1 mm). Another 1.93 g of this product was recovered from mother liquors. Silica paper chromatography revealed only one colored product.

Anal. Calcd for $C_{20}H_{12}N_6$: C, 71.41; H, 3.60; N, 24.99. Found: C, 70.77; H, 3.55; N, 24.78.

UV $\lambda_{max}^{EtOH}$: 242 nm (k 42.3), sh 252 (k 41.6), 306 (k 41.6), 427 (k 89.7).

Mass Spec.: m/e 336 (parent), 321, 244, 230.

IR: very similar to N,N-dimethyl analog plus monosubstituted benzene bands.

NMR: δ 3.47 (3.0 H singlet, N-CH₃), 6.96 (1.7 H doublet, aryl AB, J = 9 Hz), 8.07 (2.0 H doublet, aryl AB J = 9 Hz), and 7.40 (4.9 H, multiplet, $C_6H_5$).

EXAMPLE 3

6-[p-Bis[2-(benzoyloxy)ethyl]amino]phenyl-2,3,5-pyrazinetricarbonitrile

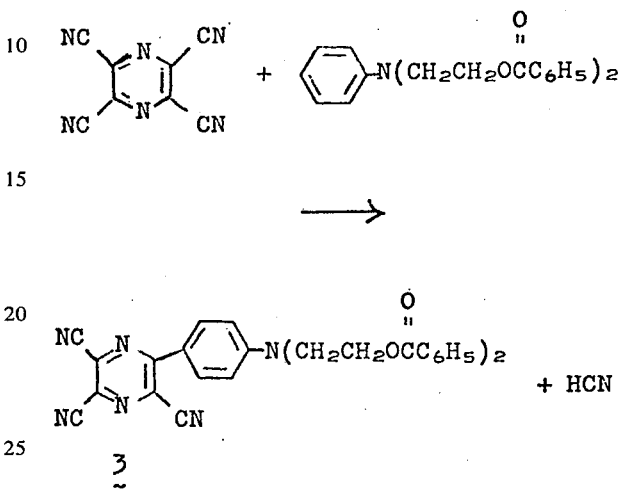

3

A mixture of 9 g (0.05 mole) of tetracyanopyrazine, 19.4 g (0.05 mole) of N,N-bis[2-(benzoyloxy)ethyl]aniline, and 100 ml of dimethylsulfoxide was heated for 18 hours at 100°C, the solution was cooled, diluted with 1 liter of ethyl acetate, and extracted with 5 liters of water. The ethyl acetate solution was dried over sodium sulfate and concentrated. The tarry residue was purified by chromatography on neutral silicic acid with hexane/benzene/ethyl acetate/ acetonitrile elution to give 12.6 g of a red fraction. Some unreacted N,N-bis[2-(benzoyloxy)ethyl]aniline was removed by hexane extraction. The remaining 10.7 g of red solid was treated with 100 ml of THF to leave 4.84 g of fairly pure product. Recrystallization from toluene gave 1.53 g of purple 6-[p-bis[2-benzoyloxy)ethyl]amino]phenyl-2,3,5-pyrazinetricarbonitrile, mp 189.6°-190.4°C. Another 4.56 g of this product was isolated from the mother liquors.

Anal. Calcd. for $C_{31}H_{22}O_4N_6$: C, 68.62; H, 4.09; N, 15.49 Found: C, 68.88; H, 4.21; N, 15.04.

IR (KBr): 3.27 μ (=CH), 3.38 (sat. C—H), 4.48 (—C ≡ N), 5.83 (C=O), 6.24, 6.62 (C=C, C=N); 12.10 (p-disubstituted aryl), 14.07 (monosubstituted aryl).

UV $\lambda_{max}^{EtOH}$: 230 nm (k 64.6), sh 2.52 (29.2), sh 262 (24.0), 305 (16.1), 422 (53.5).

NMR: calcd aryl/aliphatic, 14/8: found (less toluene) 15.0/8.0; δ 4.04 (3.7 H, N—CH₂), 4.56 (4.3 H, —OCH₂).

Mass Spec.: m/e 542 (parent), 420 (—$C_6H_5CO_2H$), 407 (—$CH_2OCOC_6H_5$), 298 (—$2C_6H_5CO_2H$), 272 (—$2CH_2OCOC_6H_5$), 244, 230.

The N,N-bis[2-(benzoyloxy)ethyl]aniline used in this example can be prepared by benzoylation of N,N-di-2-hydroxyethylaniline with benzoyl chloride as described by W. Davis and W. C. J. Ross, J. Chem. Soc., 3056 (1950).

EXAMPLE 4

6-[p-(Dimethylamino)phenyl]-2,3,5-pyrazinetricarboxamide

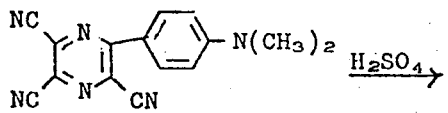

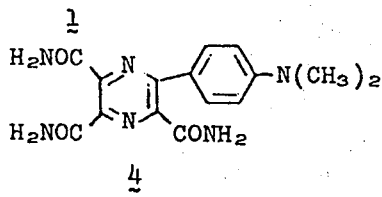

To 50 ml of concentrated sulfuric acid was added in small portions over several minutes 5 g of 1. The mixture slowly warmed to 38°C and the solid dissolved. After standing overnight at room temperature, the solution was poured onto 500 g of ice. The solution was neutralized with potassium hydroxide, then sodium carbonate to pH 8. The bright yellow precipitated solid was collected, recrystallized from boiling dimethylacetamide (decolorizing charcoal was added) and dried in a vacuum oven at 100°C to give 1.63 g of pure yellow 6-[p-(dimethylamino)phenyl]-2,3,5-pyrazinetricarboxamide, and 3.50 g of a slightly impure second crop was separated from the filtrate.

Anal. Calcd for $C_{15}H_{16}O_3N_6$: C, 54.87; H, 4.91; N, 25.60 Found: C, 53.16; H, 4.57; N, 24.62; C, 53.12; H, 4.59; N, 24.48.

IR (KBr): 2.93 $\mu$, 3.04, 3.15 ($NH_2$), 6.00 (C=O), 6.23, 6.58, 6.75 ($-NH_2$ or C=N), 12.23 p-disubstituted aryl.

UV $\lambda_{max}^{EtOH}$: 384 nm (k 52.7).

NMR: $\delta$ 3.00 (6.00 H, singlet, $NMe_2$), 6.80 (2.02 H, doublet, J = 9 Hz, aryl AB), 7.77 (doublet J = 9 $H_z$, aryl AB), 8.4, 8.12, 7.97, 7.67 (8.28 H with 7.77 peak, broad $CONH_2$ groups).

Mass Spec. (200°): m/e 328 (parent), 311.

EXAMPLE 5

6-[p-(Dimethylamino)phenyl]-2,3,5-pyrazinetricarboxylic Acid

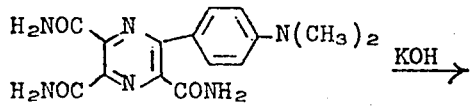

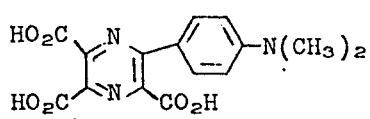

A mixture of 3.50 g (10.65 mmoles) of 4, 3.29 g (50 mmoles) of KOH pellets (85%), and 30 ml of water was heated under reflux for several hours while ammonia was swept out with a nitrogen stream until no more ammonia was detected. Then 15 ml (excess) concentrated hydrochloric acid was added and the mixture concentrated to dryness. The solid was recrystallized twice from cold water to give 2.33 g of yellow-red 6-[p-(dimethylamino)phenyl]-2,3,5-pyrazinetricarboxylic acid, mp (I) 179.1°C (dec), resolidification, mp (II), 250°–255°C (dec).

Anal. Calcd for $C_{15}H_{13}N_3O_6$: C, 54.38; H, 3.96; N, 12.69 Found: C, 53.79; H, 3.67; N, 12.49; C, 53.65; H, 3.91; N, 12.73.

IR (KBr): 5.80 $\mu$ (C=O), 6.22, 6.53 (conjugated cyclic C=C, C=N), 3.25–4.0 (OH, NH, CH).

UV $\lambda_{max}^{EtOH}$: 393 nm (k 55.2), 253 (k 33.5).

NMR: $\delta$ 7.74 and 6.83 (1.90 H and 2.10 H, doublets, and AB J = 8.5 Hz), 2.94 (6.09 H, singlet, $NMe_2$), 12.73 (3.00 H, singlet, $CO_2H$).

Utility

The novel [(p-disubstituted-amino)phenyl]-pyrazines of this invention are highly colored materials and suitable for use as dyes and pigments.

The color of the compounds of this invention is insensitive to the choice of $R^1$, $R^2$ and $R^3$. Greater variation in color is obtained in varying the X grouping from cyano to acid, amide or ester groupings.

EXAMPLE A

The novel compounds are useful as dyes, particularly for hydrophobic fibers, e.g., Dacron polyester fiber and blends of Dacron with cotton, Orlon polyacrylonitrile fiber, etc. The dyeing procedure frequently employed is the thermosol dry heat process. For example, a dye paste was prepared by sand milling a mixture of 7.6% 6-[p-bis[2-(benzoyloxy)ethyl]-amino]phenyl-2,3,5-pyrazinetricarbonitrile (3) and 15.2% lignin sulfonic acid dispersing agent in water. A sample of a 65/35 Dacron polyester/cotton blend fabric was padded at room temperature to 50% pickup, based on the dry fabric weight, in a dye bath prepared by addition of the dye paste to water at the rate of 59 g paste to 1 liter of water. The padded material was passed through an infrared predrier, dried further in a dry box at 180°F, and then heated at 415°F for 90 seconds. The fabric was then padded at 100°F in a bath containing 40 g per liter of sodium hydrosulfite and 50 g/liter of sodium hydroxide. The material was steamed for 30 seconds at 212°–220°F, rinsed in water at 80°F for 2 minutes, and oxidized for 10 minutes in a bath at 120°F containing 2.5 g/liter of sodium perborate and 1 g/liter of acetic acid. The fabric was then rinsed in water at 80°F and soaped for 5 minutes at 200°F in a bath containing 2 g/liter of a sodium ether-alcohol sulfate and 1 g/liter of sodium carbonate. Finally, the cloth was rinsed in water at 80°F and air-dried at 180°F. The cloth was dyed a deep yellow. The dye exhibited excellent sublimation fastness. In a similar manner, the substituted tricyanopyrazines, 1 and 2, were successfully used to dye the polyester in a fabric of 65/35 Dacron polyester/cotton blend.

EXAMPLE B

To a solution of 0.02 g of the tricarboxylic acid product of Example 5 in 2 ml of water was added 0.41 g of multifabric swatch. The pH was about 2 to 3. The fabric was heated at 51°C for 15 minutes, removed, rinsed three times with water and dried at 100°C in a vacuum oven. Nylon was dyed bright yellow; flanking sections of Creslan 61, Dacron 54, Dacron 64, and Orlon 75 remained white; silk was dyed medium yellow-brown; wool, yellow; acetate, Acrilan 1656 and Arnel pale yellow; cotton, Verel T5, and viscose very pale yellow.

When the pH was adjusted to above pH 11 with 0.2 ml 1N NaOH and the dyeing process repeated, no dyeing of the cloth occurred.

EXAMPLE C

A small sample of the tris-amide product of Example 4 was ground between glass plates using toluene as a lubricant. Then Datakoat (a toluene soluble, plasticized acrylic resin in a spray can by Datak Corp., Passaic, N.J.) was sprayed on the finely divided mixture and thoroughly mixed by rubbing between glass plates and scraping with a razor blade. The yellow mixture was applied to paper and dried to give a bright yellow smudge-proof finish.

The embodiments of the invention in which an exclusive property or privilege is claimed are defined as follows:

1. A compound having the formula

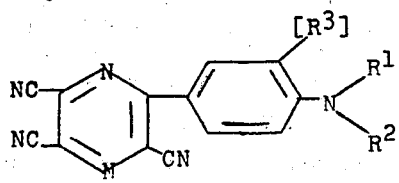

wherein:
R$^1$ and R$^2$, alike or different, are:
  alkyl of 1-12 carbon atoms, cycloalkyl of 3-7 carbons, phenyl, p-chlorophenyl, or p-bromophenyl;
  p-(lower alkyl)phenyl, p-(lower alkoxy)phenyl, or p-(lower alkylthio)phenyl, any lower alkyl being of up to 6 carbons; or
  aralkyl, aroxyalkyl, aroyloxyalkyl, alkanoyloxyalkyl or trifluoroacetoxyalkyl of up to 15 carbons with the provisos that (1) any aryl moiety in any of these five groups is phenyl substituted with up to two alkyl groups of up to six carbons each and that (2) the alkylene group of aroyloxyalkyl, alkanoyloxyalkyl or trifluoroacetoxyalkyl is of at least 2 carbons in length.

2. A compound of claim 1 wherein R$^1$ and R$^2$ are selected from alkyl of up to 6 carbons, phenyl or 2-(benzoyloxy)ethyl.

3. A compound of claim 2, 6-[-p-(dimethylamino)-phenyl]-2,3,5-pyrazinetricarbonitrile.

4. A compound of claim 2, 6-[p-(methylphenylamino)phenyl]-2,3,5-pyrazinetricarbonitrile.

5. A compound of claim 2, 6-[p-Bis[2-(benzoyloxy)ethyl]amino]phenyl-2,3,5-pyrazinetricarbonitrile.

6. A method of making a compound of claim 1 which comprises the step of contacting, in an inert solvent at a temperature in the range between 50°C and 175°C, tetracyanopyrazine with an aromatic amine of the formula:

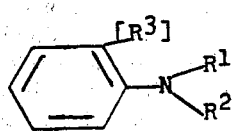

wherein R$^1$ and R$^2$ are as in claim 1.

7. The method of claim 6 wherein said reaction is conducted at a temperature in the range between 100°C and 150°C.

8. The method of claim 6 wherein tetracyanopyrazine and N,N-dimethylaniline are reacted together.

9. The method of claim 6 wherein tetracyanopyrazine and N-methyl-N-phenylaniline are reacted together.

10. The method of claim 6 wherein tetracyanopyrazine and N,N-bis[2-benzoyloxy)ethyl]aniline are reacted together.

* * * * *

UNITED STATES PATENT OFFICE
CERTIFICATE OF CORRECTION

PATENT NO. : 3,963,715
DATED : June 15, 1976
INVENTOR(S) : Donald R. Baer, Allan Cairncross & Michael Smith It is certified that error appears in the above-identified patent and that said Letters Patent are hereby corrected as shown below:

Column 15, Claim 1, in the formula "$[R^3]$" should be deleted.

Column 16, Claim 6, line 20, in the formula "$[R^3]$" should be deleted.

Signed and Sealed this

Second Day of November 1976

[SEAL]

Attest:

RUTH C. MASON
Attesting Officer

C. MARSHALL DANN
Commissioner of Patents and Trademarks